(12) United States Patent
Gudmundsson

(10) Patent No.: US 11,566,975 B2
(45) Date of Patent: Jan. 31, 2023

(54) DOSING MODULE

(71) Applicant: DELAVAL HOLDING AB, Tumba (SE)

(72) Inventor: Kristjan Freyr Gudmundsson, Tumba (SE)

(73) Assignee: DeLaval Holding AB, Tumba (SE)

( * ) Notice: Subject to any disclaimer, the term of this patent is extended or adjusted under 35 U.S.C. 154(b) by 359 days.

(21) Appl. No.: 16/769,143

(22) PCT Filed: Dec. 18, 2018

(86) PCT No.: PCT/SE2018/051338
§ 371 (c)(1),
(2) Date: Jun. 2, 2020

(87) PCT Pub. No.: WO2019/132763
PCT Pub. Date: Jul. 4, 2019

(65) Prior Publication Data
US 2020/0371003 A1    Nov. 26, 2020

(30) Foreign Application Priority Data

Dec. 28, 2017 (SE) .................... 1751662-6

(51) Int. Cl.
*G01N 1/18* (2006.01)
*G01N 35/00* (2006.01)
*G01N 1/38* (2006.01)

(52) U.S. Cl.
CPC ................. *G01N 1/18* (2013.01); *G01N 1/38* (2013.01); *G01N 35/00029* (2013.01); *G01N 2001/185* (2013.01); *G01N 2035/00108* (2013.01)

(58) Field of Classification Search
CPC .............................................. G01N 2001/185
See application file for complete search history.

(56) References Cited

U.S. PATENT DOCUMENTS

2002/0041829 A1   4/2002 Kowallis
2002/0124803 A1   9/2002 Chen et al.
(Continued)

FOREIGN PATENT DOCUMENTS

EP          0749681   * 12/1996
WO     2015/002602 A1    1/2015
(Continued)

OTHER PUBLICATIONS

International Search Report and Written Opinion, dated Feb. 27, 2019, from corresponding PCT application No. PCT/SE2018/051338.

(Continued)

*Primary Examiner* — Daniel S Larkin
(74) *Attorney, Agent, or Firm* — Nixon & Vanderhye

(57) ABSTRACT

A dosing module (137) in an agricultural environment, arranged to apply a milk sample of an animal (100) onto a dry stick (180a, 180b, 180c). The dosing module (137) includes a milk insertion connection (340) arranged to receive milk; a needle (350) configured to receive the milk and apply the received milk to the dry stick (180a, 180b, 180c); a first pump (611), configured to provide milk from the milk insertion connection (340) to the needle (350); and a position adjustment mechanism (510) configured to adjust the needle (350) between a retracted position (α) above the dry stick (180a, 180b, 180c) when dosing milk to the dry stick (180a, 180b, 180c), and at an extended position (β) when flushing milk through the needle (350); and an evacuator (195) arranged to intercept liquid output by the needle (350).

20 Claims, 8 Drawing Sheets

(56) References Cited

U.S. PATENT DOCUMENTS

| | | |
|---|---|---|
| 2005/0003522 A1 | 1/2005 | Carlsen et al. |
| 2006/0260939 A1 | 11/2006 | Anderson et al. |
| 2008/0276870 A1 | 11/2008 | Johannesson et al. |
| 2010/0326359 A1 | 12/2010 | Gudmundsson et al. |
| 2019/0082659 A1 | 3/2019 | Mottram |

FOREIGN PATENT DOCUMENTS

| | | |
|---|---|---|
| WO | 2015/008281 A1 | 1/2015 |
| WO | 2017/144913 A1 | 8/2017 |

OTHER PUBLICATIONS

SE Search Report, dated Aug. 7, 2018, from corresponding SE application No. 1751662-6.

\* cited by examiner

DOSING MODULE

TECHNICAL FIELD

This document discloses a dosing module. More particularly, a dosing module is described, arranged to apply a milk sample of an animal onto a dry stick, for enabling measurement of at least one biomarker value of a milk sample of an animal.

BACKGROUND

On an animal farm, it is important to keep the animals healthy in order to enhance milk/meat production. For example, it is important to inseminate animals at an optimal moment in order to successfully fertilise the cow. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

Thereby, a farmer/operator is provided with important information concerning each individual animal. However, to perform and analyse biomarker measurements of all individual animals at a farm, e.g. by applying milk samples on prepared dry sticks, and analyse these samples are time consuming for the farmer. It also put high demands on administrative skills on the farmer to distinguish biomarker measurements from different animals; as well as high demands on cleanliness for not allowing a biomarker measurement of a first animal to be contaminated by biological matters of another animal.

It would for these reasons be advantageous for the farmer, if the taking of biomarker measurements on milk samples of different animals could be automated, and thereby minimising or at least reducing the manual work effort of the farmer.

It would be desired to find a way to assist the farmer in analysing his/her animals and enhance production at the farm, relieving him/her from the tedious work of handling a plurality of individual dry sticks which are prepared for detecting biomarker measurements.

SUMMARY

It is therefore an object of this invention to solve at least some of the above problems and facilitate for an operator to measure a biomarker value of a milk sample of an animal.

A biomarker, or biological marker, generally refers to a measurable indicator of some biological state or condition of the animal. The biomarker value measurement may be associated with pregnancy/reproduction of the animal.

According to a first aspect of the invention, this objective is achieved by a dosing module, in an agricultural environment. The dosing module is arranged to apply a milk sample of an animal onto a dry stick. The dosing module comprises a milk insertion connection, arranged to receive milk. Further, the dosing module comprises a needle, configured to receive milk, and apply the received milk to the dry stick. Also, the dosing module comprises a first pump, configured to provide milk from the milk insertion connection to the needle. In addition, the dosing module also comprises a position adjustment mechanism, configured to adjust the needle between a retracted position above the dry stick when dosing milk to the dry stick, and at an extended position when flushing milk through the needle. The dosing module furthermore comprises an evacuator, arranged to intercept liquid output by the needle.

The dosing module is an important element for creating a modular approach in an arrangement for measuring a biomarker value of a milk sample of an animal. Different elements of the arrangement may be clustered in different modules (the cassette, the dosing module, the diluent container, the service module), having different technical lifetime intervals. The cassette may be replaced e.g. every month, the diluent container may be replaced every second month, the dosing module may be replaced once a year and the service module once every five years, for example. Thereby, a continuous, automatic test of the biological marker may be made, with a minimal additional work of the operator.

In a first possible implementation of the dosing module according to the first aspect, the dosing module may comprise a dilutant insertion connection, arranged to receive dilutant. Further, the dosing module may comprise a mixing chamber, arranged to receive milk from the liquid insertion connection and dilutant from the dilutant insertion connection. In addition, the dosing module also may comprise a second pump, configured to provide dilutant from the dilutant insertion connection to the mixing chamber. The first pump is configured to provide milk from the milk insertion connection to the mixing chamber. Also, the needle is configured to receive a mixture of milk and dilutant from the mixing chamber, and apply the mixture to the dry stick.

In a second possible implementation of the dosing module according to the first aspect, or according to the first possible implementation thereof, the dry stick may be comprised on a tape of a cassette. Also, the needle may be configured to be inserted in an aperture of the cassette.

In a third possible implementation of the dosing module according to the first aspect, or according to any previously disclosed possible implementation thereof, the milk insertion connection is arranged to receive milk from a milk line of milking equipment. The dosing module comprises a return conduit, arranged to convey liquid from the evacuator back to the milk line, a waste container or drain.

Thereby, thanks to the evacuator and the return conduit of the dosing module, it becomes possible to rinse the needle between application of milk samples from different animals, without risk of contamination of other, yet unused dry sticks on the tape.

In a fourth possible implementation of the dosing module according to the first aspect, or according to any previously disclosed possible implementation thereof, the first pump, and/or the second pump may comprise a positive displacement pump.

In a fifth possible implementation of the dosing module according to the first aspect, or according to any previously disclosed possible implementation thereof, the first pump, and/or the second pump may comprise a peristaltic pump.

In a sixth possible implementation of the dosing module according to the first aspect, or according to any previously disclosed possible implementation thereof, the position adjustment mechanism may be configured to cooperate with an external linear motor.

Thereby, the linear motor may be kept in the service module while only disposable components, such as pumps, evacuator, tubings, etc.

In a seventh possible implementation of the dosing module according to the first aspect, or according to any previously disclosed possible implementation thereof, the position adjustment mechanism may comprise a ball joint.

In an eighth possible implementation of the dosing module according to the first aspect, or according to any previously disclosed possible implementation thereof, the dosing module may comprise detachably arranged fastening means, arranged to attach the dosing module onto a service module, into which the cassette is insertable.

Thereby an easy exchange of the dosing module is ascertained.

In a ninth possible implementation of the dosing module according to the first aspect, or according to any previously disclosed possible implementation thereof, the fastening means may comprise a snap fit arrangement.

In a tenth possible implementation of the dosing module according to the first aspect, or according to any previously disclosed possible implementation thereof, the dosing module may comprise a first cover section and a connected second cover section, enclosing the first pump, the second pump, the evacuator, and tubings.

The plastic tubings may over time get aged and affected by the milk. For this reason, they are to be exchanged at a regular time interval, such as once each year, once every six months, etc., together with the needle the other parts of the dosing module.

In an eleventh possible implementation of the dosing module according to the first aspect, or according to any previously disclosed possible implementation thereof, the first cover section and the second cover section may be made of plastic.

In a twelfth possible implementation of the dosing module according to the first aspect, or according to any previously disclosed possible implementation thereof, the dosing module may form a disposable unit.

Thanks to the described aspects, by determining biomarker values of milk samples of animals on the farm, various states, e.g. related to reproduction of the animals, or various deceases or other anomalies may be determined. By keeping the arrangement modular in form of the dosing module, the service module and the cassette, which may be attached to milking equipment of the farm; costs, maintenance and work intensity of the operator may be minimised or at least reduced. Also, by separating the consumable material, such as measurement sticks of the cassette, from elements subject to wear, like the pumps of the dosing module, and the electronics and instruments of the service module; the dosing module could be continuously replaced with another replacement dosing module e.g. via a courier service or postal office subscription.

The service module may on the other hand be detached from the milking equipment and the dosing module; and sent to a workshop for troubleshooting, repair, maintenance, etc. Meanwhile, an identical replacement service module may be provided to the farm, enabling continuous biomarker measurements on the farm, also when the equipment of the service module is malfunctioning. Further, the arrangement may be operated by the operator without requiring a technician to come and visit the farm. Instead, the operator may send the malfunctioning service module to the workshop.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a dosing module, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
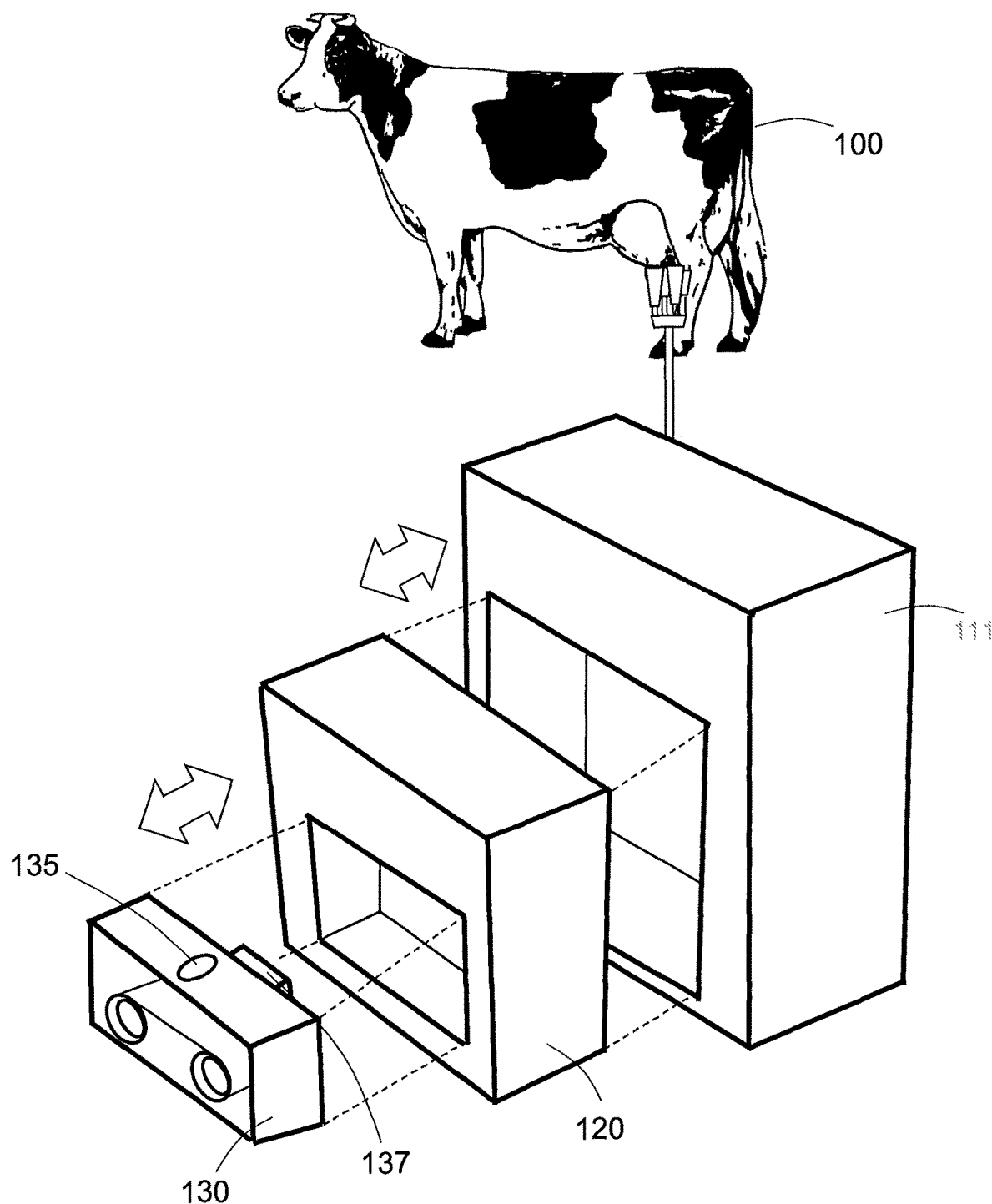
FIG. 1 illustrates an example of an arrangement for measuring a biomarker value of a milk sample of an animal.

FIG. 1 illustrates a scenario with an animal 100 which may be comprised in a herd of dairy animals at a dairy farm.

"Animal" may be any arbitrary type of domesticated female milk producing and/or meat producing mammal, such as cow, goat, sheep, horse, camel, primate, dairy buffalo, donkey, yak, etc.

Milk of the animal 100 may be extracted by milking equipment, such as e.g. a milking robot or other milking arrangement, and provided to a service module 120.

The service module 120 may be releasably inserted into the milking equipment in some embodiments. Thus, there may be an interface between the milking equipment and the service module 120 for providing milk and possibly electricity via the milking equipment to the service module 120.

The service module 120 may be releasably inserted into a portion 111 of the milking equipment in some embodiments. Thus, there may be an interface between the milking equipment and the service module 120 for providing milk and possibly electricity via the milking equipment to the service module 120.

The service module 120 comprises various electronics and equipment, such as a camera, one or several pumps, a tube element for attachment to the interface to the milking equipment, motors, a communication unit etc.

A cassette 130 may be detachably inserted into the service module 120. The cassette 130 comprises a tape with dry sticks, configured to indicate a biomarker value of a milk sample of the animal 100. The cassette 130 may in some embodiments be configured to be detachably inserted in the service module 120 and held in place by a fastening means, such as a snap lock, a magnet, a screw, etc., and a door of the service module 120 may be closed for enclosing the cassette 130 within the service module 120, thereby further fixating the cassette 130 in the position.

Thereby, a milk sample of the animal 100 may be extracted from the animal 100 by the milking equipment and provided via the service module 120 to one of the dry sticks on the tape of the cassette 130. The dry sticks may react on presence and/or amount of one or several biomarkers, e.g. by changing colours, or intensity of a colour. The camera in the service module 120 may capture an image through an opening 135 in the cassette 130. The captured image of the dry sticks may then be analysed by a control unit, and based on the intensity of the colour, presence and/or quantity of the biomarker in the milk sample may thereby be determined.

The measured biomarker may be e.g. progesterone, glycoprotein, oestrogen and/or Gonadatropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing *oestrus* and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the operator to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the operator may subscribe to the cassette 130 comprising a certain dry stick on a tape configured to measure a biomarker, or a set of biomarkers, as selected by the farmer; and/or different cassettes 130 comprising dry sticks on the tape configured to measure different biomarkers, or sets of biomarkers, during different periods of time of the year.

In some embodiments, a dosing module 137 may also be detachably inserted into the service module 120. The dosing module 137 may comprise, for example a needle, and/or one or several pumps. A diluent container with diluent may be external to the dosing module 137.

Figure 2A:
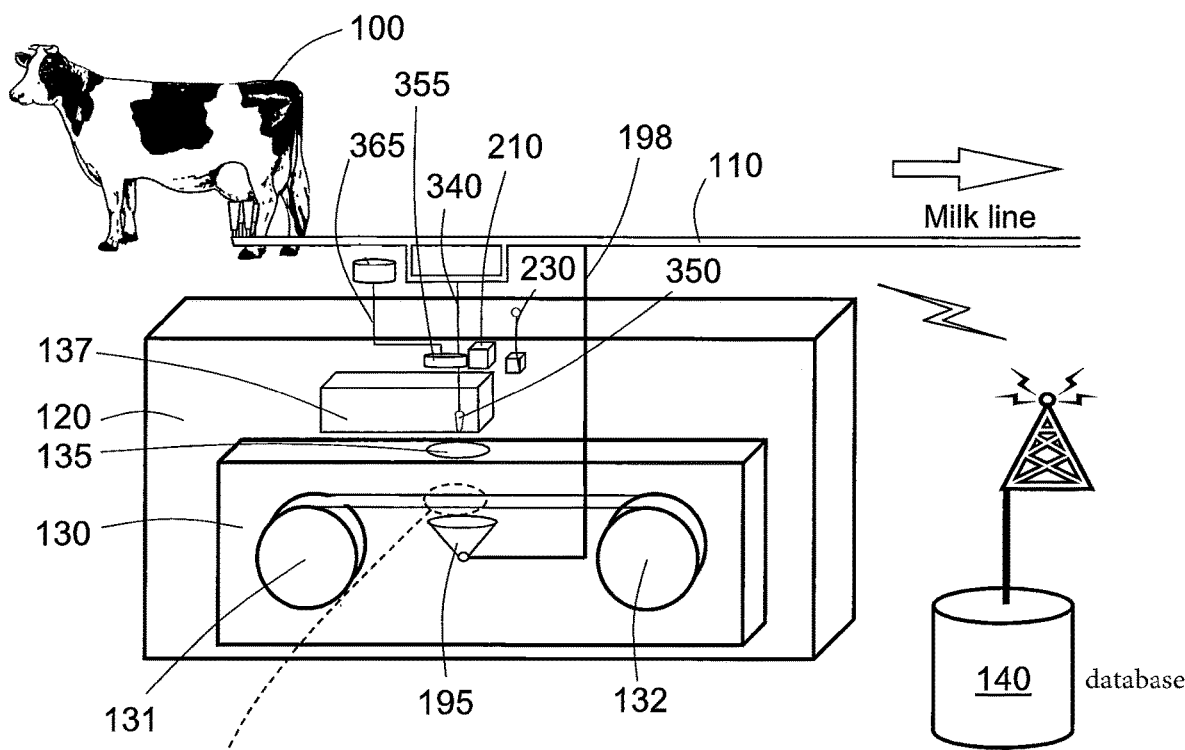
FIG. 2A illustrates a cassette inserted into a service module, according to an embodiment.

FIG. 1 and FIG. 2A depict general overviews of the environment in which the tape according to the provided solution is intended to operate, without going too much into details, in order for the reader to get a rough overview. Sublime examples of details of the tape may be studied in FIG. 2B. FIG. 3 illustrates the cassette 130, as regarded from behind, while FIG. 4, FIG. 5, FIG. 6, FIG. 7A, and FIG. 7B illustrates the dosing module 137 as regarded from different views.

FIG. 2A illustrates a scenario illustrating the service module 120, the cassette 130, and a dosing module 137 interacting with each other, according to an embodiment. The service module 120 may comprise electronics and equipment, such as e.g. a camera 210, a tube element 340 for attachment to the milking equipment, a motor, a communication unit 230, etc., to be used for determining a biometric value of a milk sample received from an animal 100. In some embodiments, the dosing module 137 may comprise one or several pumps configured to act on the tube element 340 for advancing the milk sample from the milking equipment through the tube element 340.

In the illustrated embodiment, the dosing module 137 may comprise a needle 350 for applying the milk sample to a dry stick 180a, 180b, 180c on a tape 170 in the cassette 130 through an opening 135 in the cassette 130. The camera 210 may then align the needle 350 with one of the dry sticks 180a, 180b, 180c on the tape 170 of the cassette 130.

The camera 210 of the service module 120 may capture an image of the dry sticks 180a, 180b, 180c of the carrier tape 170 through the opening 135, and based on these images, a cassette external motor may adjust the tape 170 for positioning new dry sticks 180a, 180b, 180c, on which a new test is to be made, in relation to the needle 350.

The communication unit 230 may communicate via a wired or wireless communication interface, with a control unit 150, a database 140, and/or an output unit 160.

Such wireless communication interface may comprise, or at least be inspired by wireless communication technology, such as Wi-Fi, 3GPP LTE, Bluetooth (BT) to name but a few possible examples of wireless communications in some embodiments.

The camera 210 of the service module 120 is configured to inspect one dry stick 180a, 180b, 180c on the tape 170 of the cassette 130, through the opening 135 of the cassette 130. The camera 210 may also assist in alignment of the needle 350 and the position of the one dry stick 180a, 180b, 180c on the tape 170, by adjusting the tape 170.

Further, the service module 120 also comprises a tube element 340 configured to receive the milk sample of the animal 100 via milking equipment and provide the milk sample to a needle 350, i.e. the needle 350 comprised in the dosing module 137.

The dosing module 137 may in addition comprise at least one pump in some embodiments, configured to act on the tube element 340 for providing the milk sample to the needle 350. The pump may thus act on the tube element 340 to get the milk sample to propagate through the tube element 340 to reach the needle 350; or a mixing chamber 355 of the needle 350. The mixing chamber 355 may alternatively be external to the needle 350.

The dosing module 137 may also comprise a liquid evacuator or drainage 195, which may collect liquid that has been output by the needle 350. The liquid, when comprising merely milk, may be returned back 198 to the milk line 110 in some embodiments. In other embodiments, when the milk has been mixed with diluent, the liquid may be conveyed away from the cassette 130 in order not to soak or contaminate other, unused, dry sticks 180a, 180b, 180c of the tape 170 on the cassette 130.

The control unit 150 is configured to determine a biomarker value of the milk sample of the animal 100, based on an analysis of the image, captured by the camera 210. The control unit 150 may be comprised in the service module 120 in some embodiments; or be external to the service module 120.

The database 140 may store measured biometric values of the animal 100, associated with an identity reference of the animal 100 and/or a time stamp of the measurement. Other measurements and/or data related to the animal 100 may also be stored in the database 140, such as milk yield, e.g. measured by the milk flow meter, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, an operator may take part of the result of the biomarker measurement of the milk sample. The operator is thereby able to analyse the status of the animal 100, such as e.g. if the animal 100 is in heat, in case progesterone is measured.

When a deviation, exceeding a first threshold limit, is detected between the outcomes of the biomarker measurement and the corresponding reference value, an alert may be outputted to the operator. The alert may comprise e.g. visual information, an audio message, a tactile signal or a combination thereof, encouraging the operator to further investigate the reasons for the detected deviation in result. In case a plurality of people is working with the herd, a broadcast may be made to the plurality of operators and their respective associated output units 160, in some embodiments.

Figure 2B:
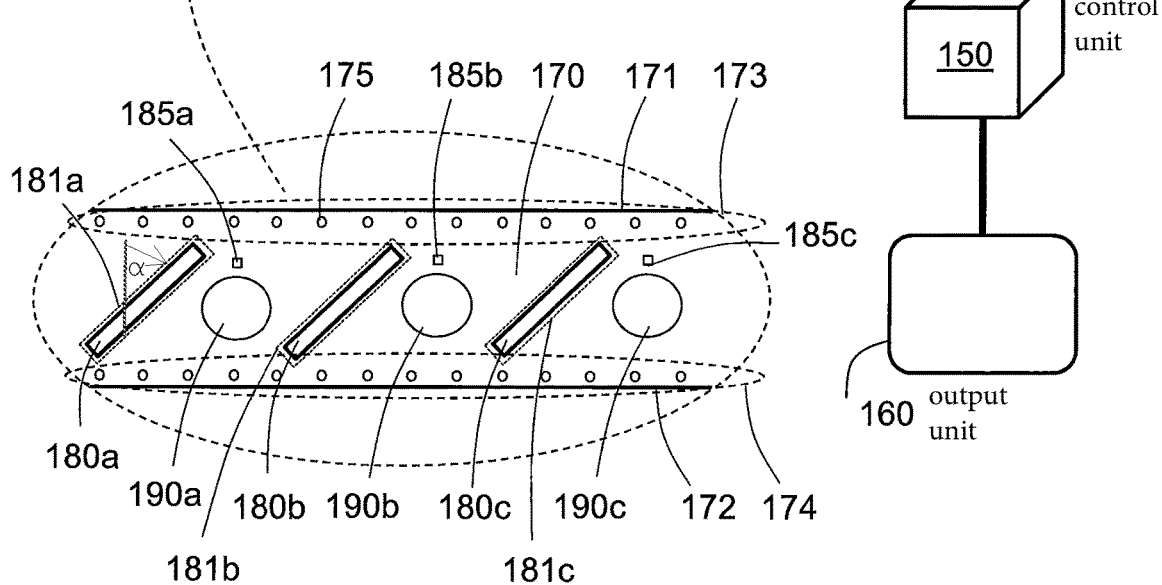
FIG. 2B illustrates a section of a tape comprising dry sticks, according to an embodiment.
Figure 3:
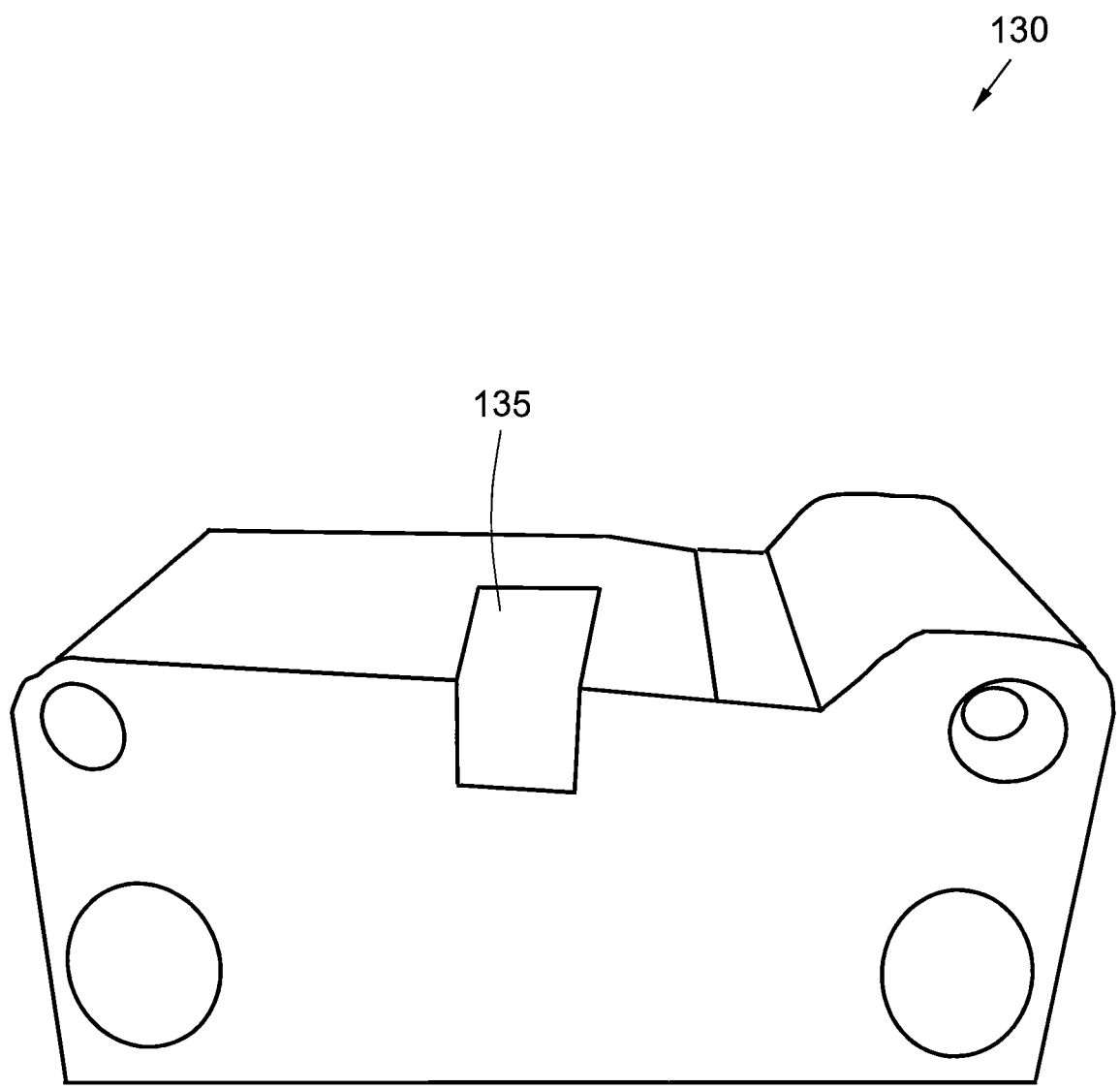
FIG. 3 illustrates a cassette, according to an embodiment.

FIG. 2B illustrates a tape 170 according to an embodiment. The cassette 130, which may be releasably inserted into the service module 120, comprises the tape 170, which in turn comprises a plurality of dry sticks 180a, 180b, 180c.

The dry sticks 180a, 180b, 180c may be arranged with an inclination a in relation to an axis, orthogonal to a longitudinal axis of the tape 170. The inclination a may, for example be 15 degrees or there about, or e.g. 10-30 degrees in some embodiments.

An opening 190a, 190b, 190c, may be arranged between at least some of the dry sticks 180a, 180b, 180c, on the tape 170, or on a bottom film of the tape 170, i.e. between the welded seams 181a, 181b, 181c of at least some of the dry sticks 180a, 180b, 180c on the bottom film. The openings 190a, 190b, 190c are configured to convey liquid away from the dry sticks 180a, 180b, 180c during cleaning, or before applying the milk sample to the dry sticks 180a, 180b, 180c.

Milk of a first animal 100 may contaminate a milk sample of another, subsequently tested animal. To avoid contamination, or carry over, the tubings and the needle 350 may be flushed with milk of the animal to be tested before the milk sample is applied to the dry sticks 180a, 180b, 180c. For avoiding that the flushed milk of the animal to be tested soaks and/or contaminate other unused dry sticks 180a, 180b, 180c, the flushing may be made through the openings 190a, 190b, 190c of the tape 170, e.g. by lowering the needle 350 through the openings 190a, 190b, 190c, and capture the flushed milk with a liquid evacuator 195. The liquid evacuator 195 may then via a tube 198 convey liquid away from the cassette 130.

The tape 170, or the bottom film of the tape 170 may further comprise a reference mark 185a, 185b, 185c, configured to assist the camera 210 in finding the dry sticks 180a, 180b, 180c. The reference marks 185a, 185b, 185c may comprise e.g. a hole, a colour mark, a barcode, a simple geometry, or similar.

The reference marks 185a, 185b, 185c may also assist the camera 210 in determining the advancement of the top film reel, to peel off the top film of the dry sticks 180a, 180b, 180c, enough to enable application of the milk sample to the dry sticks 180a, 180b, 180c, while not peeling off the top film of the next dry sticks 180a, 180b, 180c.

Further, with additional reference to FIG. 2A, the tape 170, or the bottom film of the tape 170 may comprise a first group 173 of advancement apertures 175, arranged at a first edge 171 of the tape 170; and a second group 174 of advancement apertures 175, arranged at a second edge 172 of the tape 170, or the bottom film of the tape 170.

Each dry stick 180a, 180b, 180c may be separately arranged on the tape 170, or the bottom film of the tape 170, by a welded seam 181a, 181b, 181c, and wherein the sealed dry sticks 180a, 180b, 180c are arranged at a distance from each other.

FIG. 3 illustrates a cassette 130, comprising the opening 135, as regarded from the rear side of the cassette 130 when inserted into the service module 120.

The tape 170 may be arranged on a tape distributing spool 131 and a tape collecting spool 132 of the cassette 130, which spools 131, 132 may be arranged in the cassette 130, and be configured to cooperate with at least one cassette external motor for positional adjustment of the carrier tape 170. The cassette external motor may be comprised in the service module 120 in some embodiments. The cassette external motor may actuate on a capstan reel and/or a top film reel. Further, a driving belt may be applied on the capstan reel and at least one of the spools 131, 132 for conveying driving motion of the cassette external motor, via the capstan reel and the driving belt, to the spools 131, 132. In some embodiments, the driving belt may be arranged to convey driving motion from the capstan reel to the tape collecting spool 132. Thereby, the position of the dry sticks 180a, 180b, 180c on the tape 170 in relation to the opening 135 may be adjusted by advancing the tape 170 via the cassette external motor or motors, by rotating the tape collecting spool 132 of the cassette 130.

Figure 4:
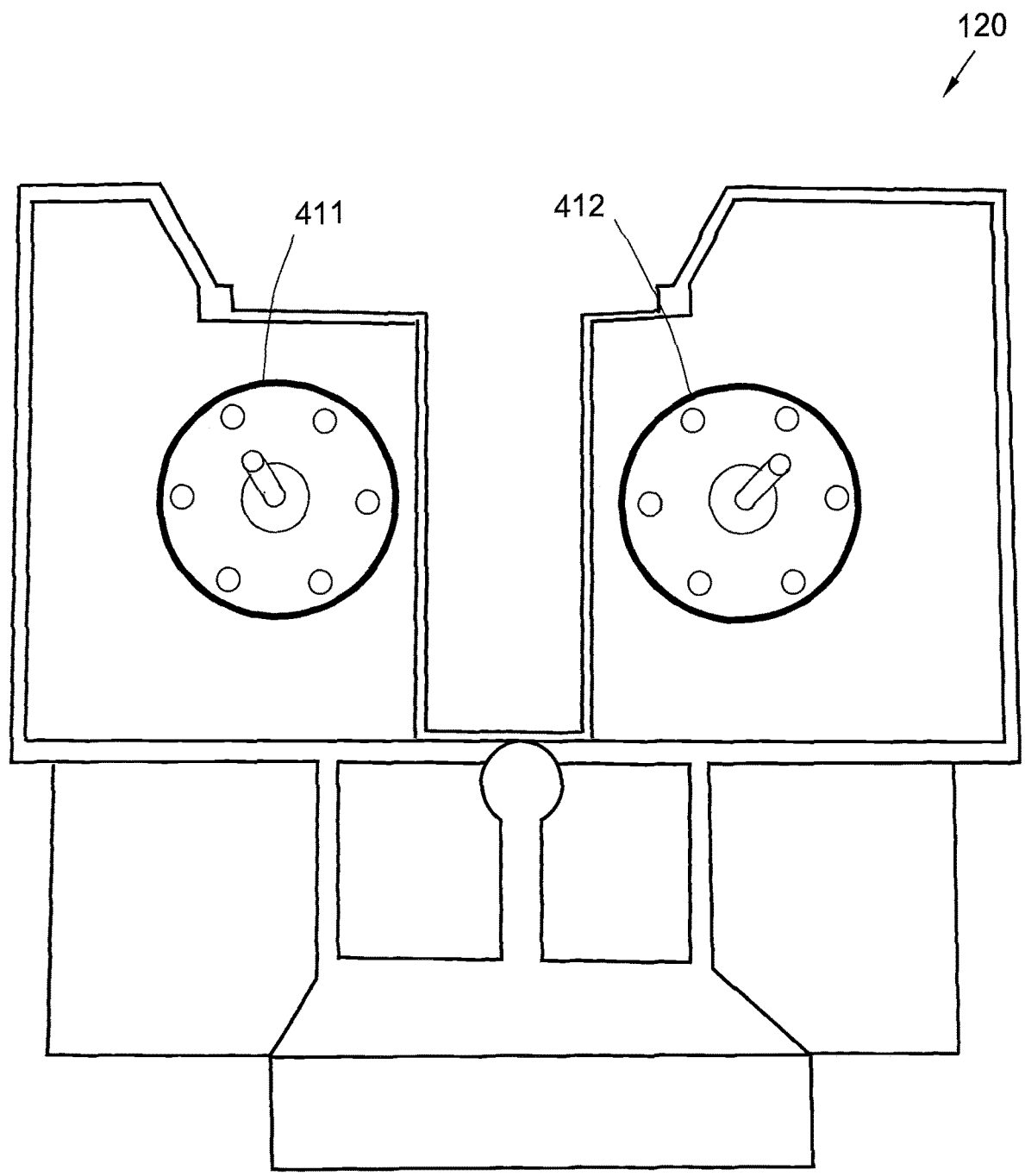
FIG. 4 illustrates a view of a service module, according to an embodiment.

FIG. 4 illustrates the service module 120, comprising a first pump motor 411 and a second pump motor 412, in the illustrated embodiment, as regarded from behind.

The dosing module 137 may be inserted from the back onto the service module 120, and the axle of the first pump motor 411 may be inserted into the first pump of the dosing module 137 while the axle of the (optional) second pump motor 412 may be inserted into the second pump of the dosing module 137. The dosing module 137 thereby fixates the motors 411, 412 when it is inserted in operational position.

An advantage with keeping the pump motors 411, 412 in the service module 120 while keeping the pumps in the dosing module 137 is that the dosing module 137 with the pumps (which are subject to wear) may be regularly replaced, e.g. once a year, every 18 months, etc., while the more expensive parts, having a longer technical service life, such as the pump motors 411, 412 may be maintained in the service module 120, and only be replaced upon malfunction in some embodiments.

In case of malfunction, the dosing module 137 may be replaced instantly.

The dosing module 137 may be disposable, when the service period of the dosing module 137 has reached an end and the dosing module 137 has been replaced.

Figure 5:
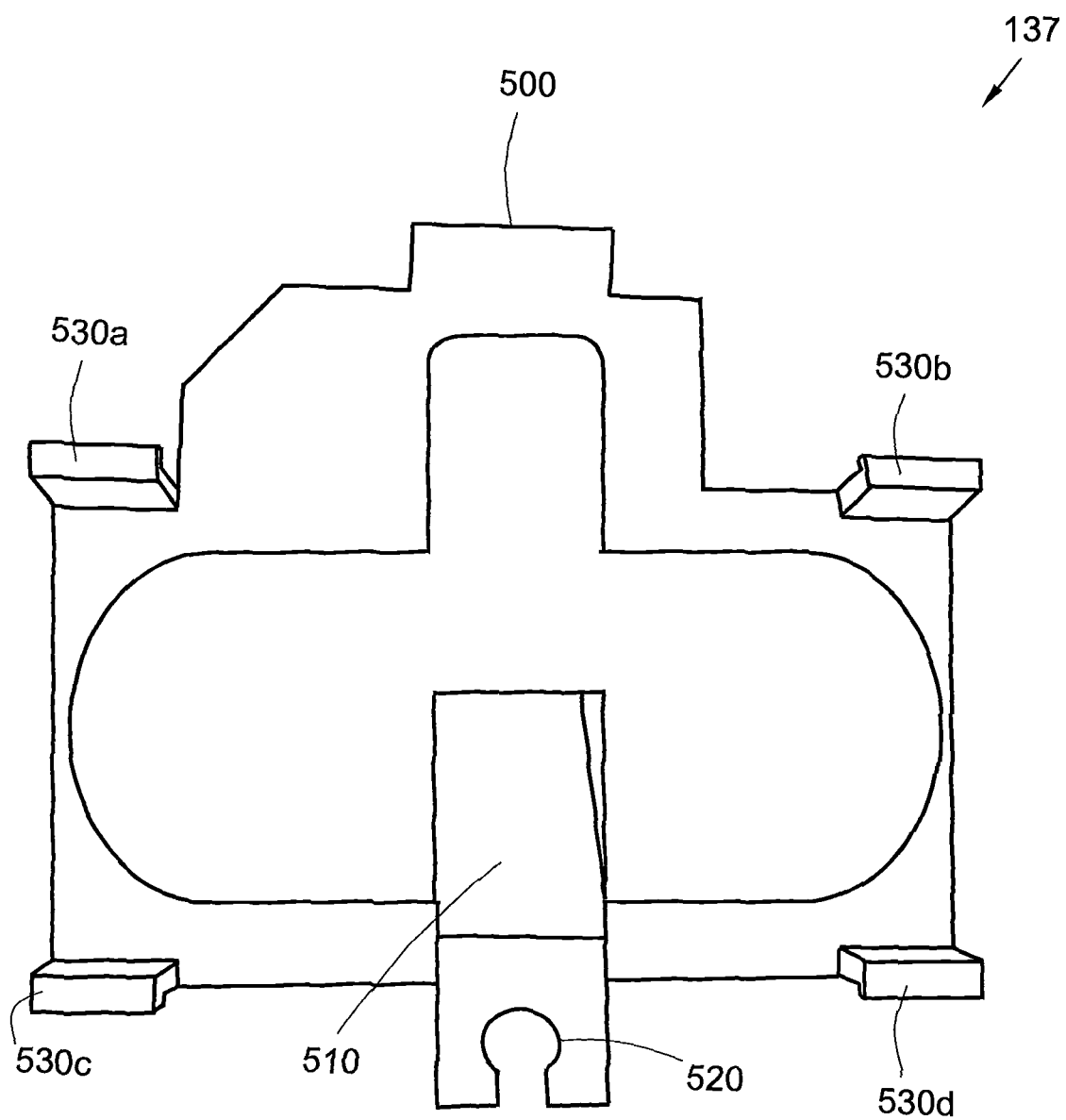
FIG. 5 illustrates a view of a dosing module, according to an embodiment.

FIG. 5 illustrates a dosing module 137, or a first cover section 500, or cover shield, of the dosing module 137. The first part 500 may be made of plastic, such as e.g. polyamide, polycarbonate, polyethylene, polypropylene, polyvinylchloride, etc., and may cover the interior of the dosing module 137.

In FIG. 5, a position adjustment mechanism 510 may be observed, having a ball joint 520, to be connected to a linear motor.

The first part 500 may also comprise fastening means 530a, 530b, 530c, 530d, e.g. in form of a snap fit arrangement, magnetics, screw joints, etc., arranged to attach the dosing module 137 onto the service module 120.

Figure 6:
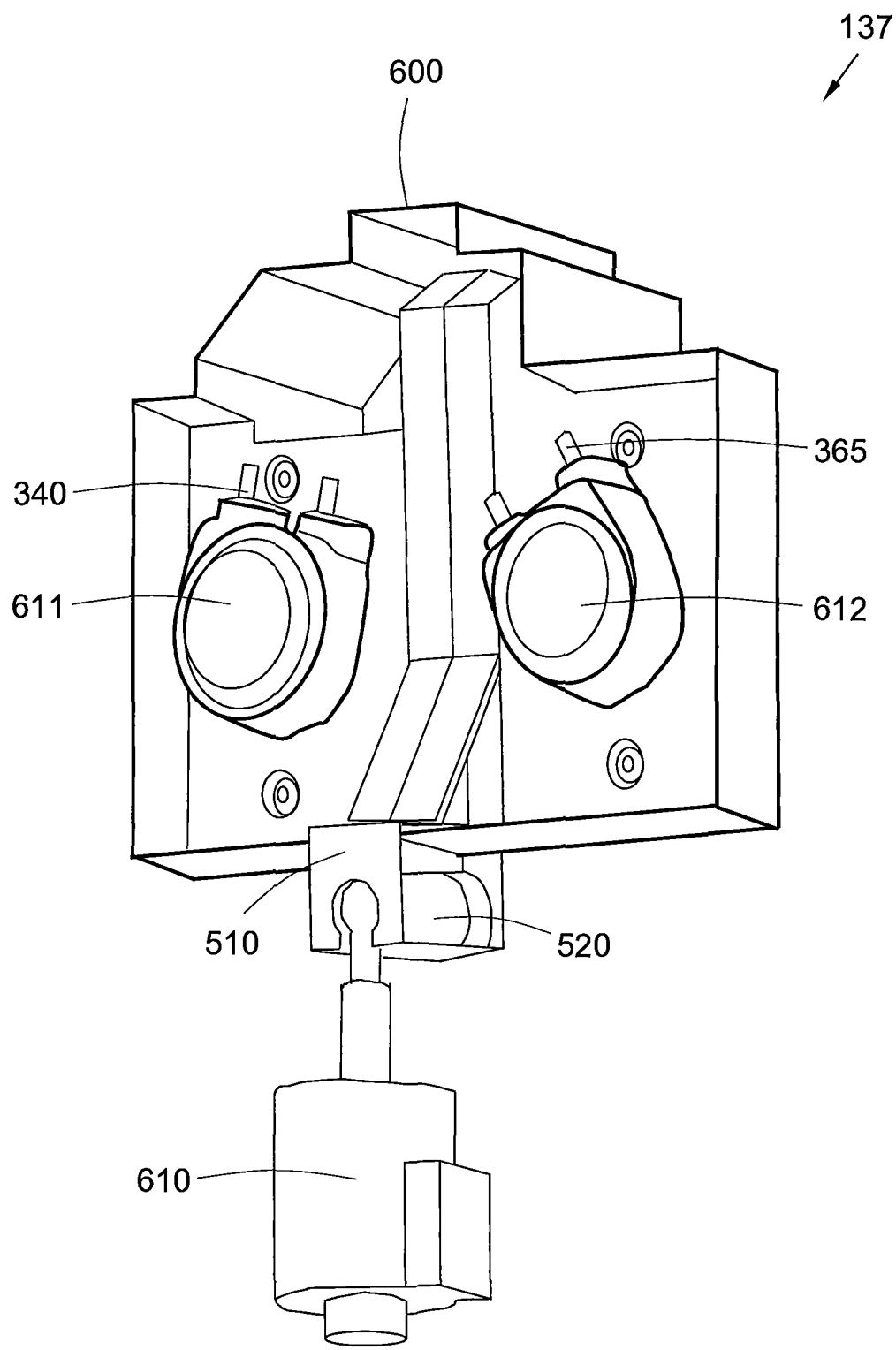
FIG. 6 illustrates a view of a dosing module, according to an embodiment.

FIG. 6 illustrates a second cover section 600, illustrating the interior of the dosing module 137, onto which the first cover section 500 is to be mounted to complete the dosing module 137.

The dosing module 137 comprises a milk insertion connection 340, arranged to receive milk from milking equipment. Further, the dosing module 137 comprises a first pump 611, configured to provide milk from the milk insertion connection 340 to the needle 350 of the dosing module 137.

In some embodiments, the dosing module 137 also may comprise a dilutant insertion connection 365, arranged to receive dilutant. Further, the dosing module 137 may comprise a mixing chamber 355, arranged to receive milk from the liquid insertion connection 340 and dilutant from the dilutant insertion connection 365. The dosing module 137 may also comprise a second pump 612, configured to provide dilutant from the dilutant insertion connection 365 to the mixing chamber 355.

The first pump 611 may be driven by the first pump motor 411 of the service module 120, while the optional second pump 612 may be driven by the second pump motor 412 of the service module 120.

The first pump 611 and/or the second pump 612 may comprise a positive displacement pump, such as a peristaltic pump, which also may be referred to as a hose pump, a tube pump and/or a microfluidic pump.

The fluid, such as milk or dilutant, is comprised within a flexible tube fitted inside a respective circular pump casing of the first pump 611 and/or the second pump 612. A rotor with a number of "rollers", "shoes", "wipers", or "lobes" attached to the external circumference of the rotor compresses the flexible tube. As the rotor turns, the part of the tube under compression is pinched closed thus forcing the fluid to be pumped to move through the tube. Additionally, as the tube opens to its natural state after the passing of the cam ("restitution" or "resilience") fluid flow is induced to the pump, 611, 612. This process may be referred to as peristalsis. Typically, there may be two or more rollers, or wipers, occluding the tube, trapping between them a body of fluid. The body of fluid is then transported, at ambient pressure, toward the pump outlet. The pumps 611, 612 may run continuously in some embodiments, or they may be indexed through partial revolutions to deliver smaller amounts of fluid, such as e.g. some millilitres.

An advantage with using peristaltic pumps 611, 612 is that contamination is avoided, as the only part of the pump 611, 612 in contact with the milk being pumped is the interior of the tube, it is easy to sterilise and clean the inside surfaces of the pump 611, 612. Another advantage is that the pumps 611, 612 require only very low, if any, maintenance as the pumps 611, 612 lack valves, seals and glands, etc.

The position adjustment mechanism 510 may be configured to cooperate with a linear motor 610 in some embodiments, for adjusting the position adjustment mechanism 510, adjusting the position of the needle 350. The movement may be a linear movement, or a lever movement. The linear motor 610 may be comprised in the service module 120, for example.

Figure 7A:
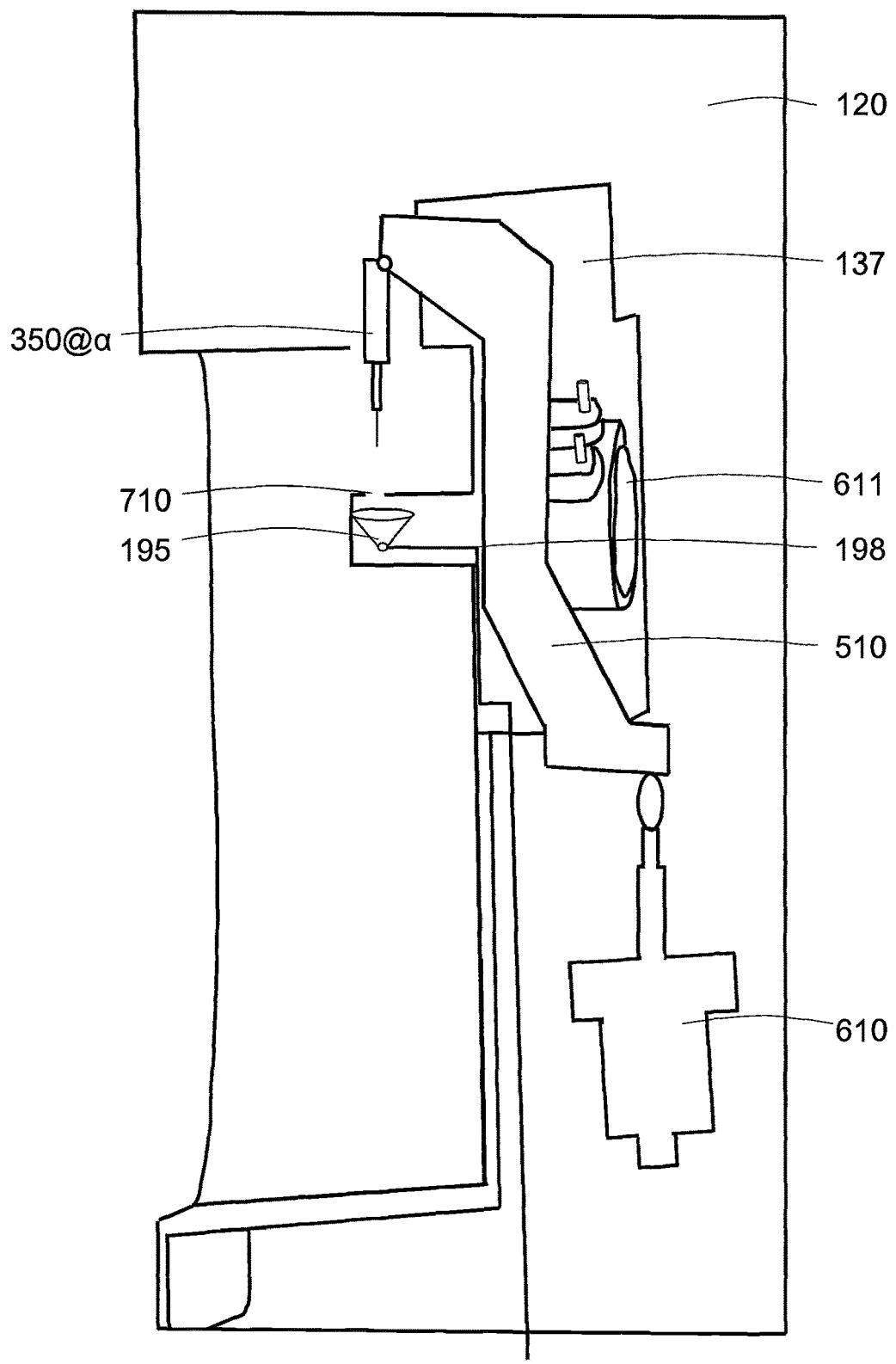
FIG. 7A illustrates a view of a dosing module, according to an embodiment.
Figure 7B:
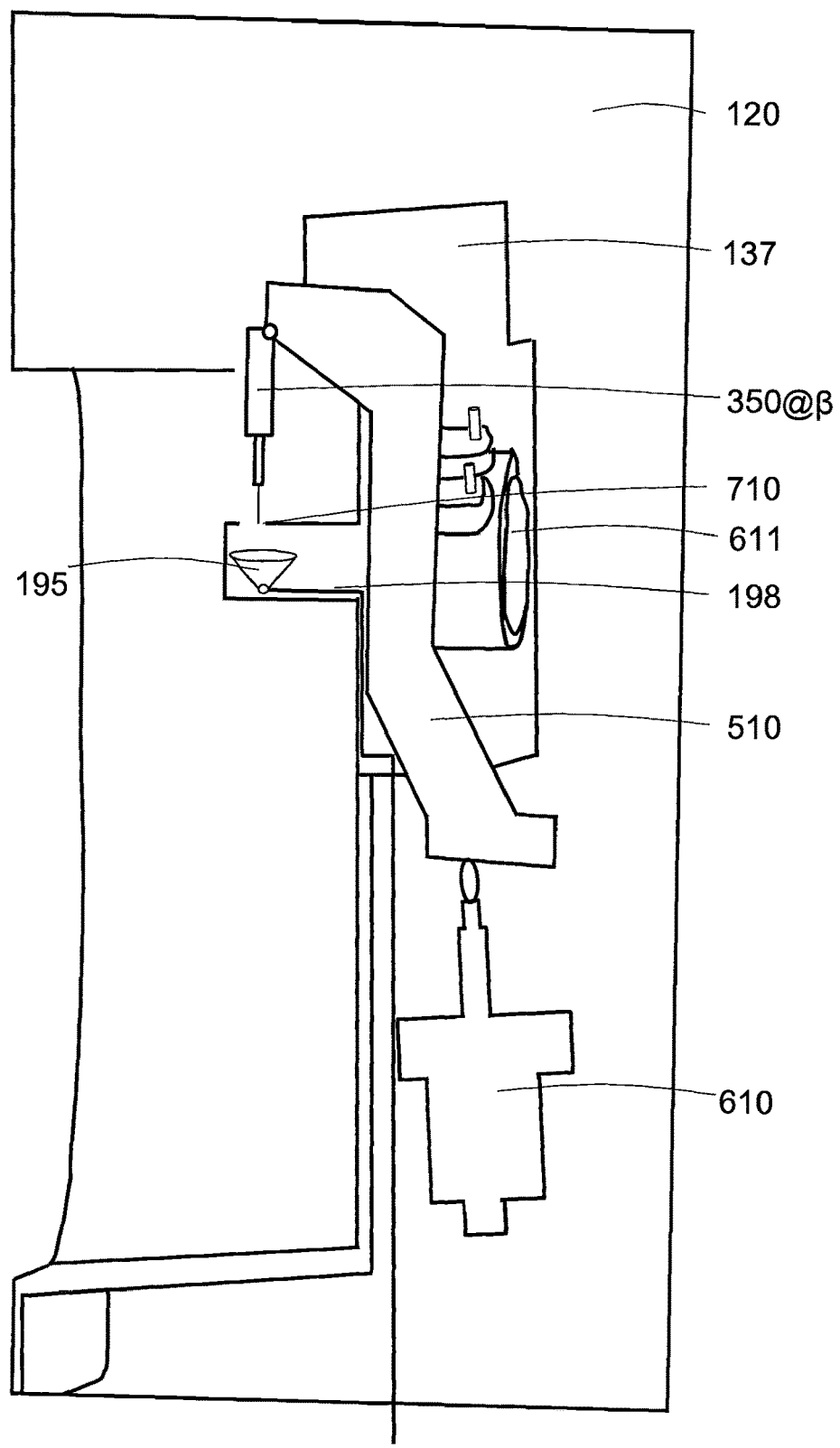
FIG. 7B illustrates a view of a dosing module, according to an embodiment.

FIG. 7A and FIG. 7B illustrate a dosing module 137 as regarded from the side.

The position adjustment mechanism 510 is configured to adjust the needle 350 between a retracted position α above the dry sticks 180a, 180b, 180c when dosing milk to the dry sticks 180a, 180b, 180c, as illustrated in FIG. 7A, and at an extended position β when flushing milk through the needle 350, as illustrated in FIG. 7B.

The position adjustment mechanism 510 may forward a movement of the linear motor 610, to the needle 350. The needle 350 may thereby be positioned in a retracted position when applying milk to the dry sticks 180a, 180b, 180c, and in an extended position lowering the needle 350 down to an opening 190 in the tape 170.

In FIG. 7A, the motor 610 has extended the position adjustment mechanism 510, and thereby also the needle 350 up to the retracted position a. This is the position kept when the needle 350 is to apply a milk sample to the dry sticks 180a, 180b, 180c, on the tape 170.

In FIG. 7B, the motor 610 has lowered the position adjustment mechanism 510, and thereby also the needle 350 down to the extended position α. This is the position kept when the needle 350 is to be rinsed between milk samples of different animals 100. The needle tip may be lowered under the dry sticks 180a, 180b, 180c through the hole 190 in the tape 170, and the liquid may be conveyed away from the cassette 130 via the evacuator 195 and the return conduit 198, arranged to evacuate liquid from the aperture 710 back to the milk line 110, waste container, or drain.

The embodiments, or parts thereof, illustrated in FIG. 1, FIG. 2A, FIG. 2B, FIG. 3, FIG. 4, FIG. 5, FIG. 6, and/or FIG. 7A-FIG. 7B may with advantage be combined with each other for achieving further benefits.

The terminology used in the description of the embodiments as illustrated in the accompanying drawings is not intended to be limiting of the described dosing module 137. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit, such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms, such as via Internet or other wired or wireless communication system.

The invention claimed is:

1. A dosing module (137) in an agricultural environment, the dosing module (137) arranged to apply milk of an animal (100) onto a dry stick (180a, 180b, 180c) as a milk sample, the dosing module (137) comprising:

a cover comprising a first cover section (500) and a second cover section (600), the first and second cover sections (500, 600) defining an interior space within the cover of the dosing module, the cover being mountable within a service module (120) that includes a cassette (130) housing the dry stick (180a, 180b, 180c);
a milk insertion connection (340) arranged to receive the milk sample;
a needle (350) configured to receive the milk sample from the milk insertion connection (340) and, with the cover mounted in the service module (120), apply the milk sample to the dry stick (180a, 180b, 180c);
a first pump (611) configured to provide the milk sample from the milk insertion connection (340) to the needle (350);
a position adjustment mechanism (510) located within the interior space of the cover, the position adjustment mechanism (510) being connected to the needle (350) and having a motor connection (520),
wherein with the cover mounted in the service module (120), movement of the motor connection (520) moving the position adjustment mechanism (510) between a first position and a second position adjusts a position of the needle (350) between a retracted position (α) above the dry stick (180a, 180b, 180c) for dosing the milk sample to the dry stick (180a, 180b, 180c) and an extended position (β) for flushing the milk sample through the needle (350); and
an evacuator (195) located within the interior space of the cover, the evacuator (195) arranged to extend into the cassette to intercept liquid output by the needle (350) when the position adjustment mechanism (510) is in the second position that adjusts the needle (350) into the extended position (β).

2. The dosing module (137) according to claim 1, further comprising:
a dilutant insertion connection (365) arranged to receive dilutant;
a mixing chamber (355) arranged to receive the milk sample from the milk insertion connection (340) and receive the dilutant from the dilutant insertion connection (365); and
a second pump (612) configured to provide the dilutant from the dilutant insertion connection (365) to the mixing chamber (355), wherein,
the first pump (611) is configured to provide the milk sample from the milk insertion connection (340) to the mixing chamber (355), and
the needle (350) is configured to receive a mixture of the milk sample and the dilutant from the mixing chamber (355), and apply the mixture to the dry stick (180a, 180b, 180c).

3. The dosing module (137) according to claim 2, wherein at least one of the first pump (611) and the second pump (612) comprises a positive displacement pump.

4. The dosing module (137) according to claim 3, wherein at least one of the first pump (611) and the second pump (612) comprises a peristaltic pump.

5. The dosing module (137) according to claim 2, wherein the first cover section (500) is connected to the second cover section (600), the first and second cover sections (500, 600) enclosing the first pump (611), the second pump (612), the evacuator (195), and tubings.

6. The dosing module (137) according to claim 5, wherein the first cover section (500) and the second cover section (600) are made of plastic.

7. The dosing module (137) according to claim 5, forming a disposable unit.

8. The dosing module (137) according to claim 1 in combination with the cassette (130) housing the dry stick (180a, 180b, 180c),
wherein the cassette (130) is comprised of a housing having an aperture (135),
wherein the cassette (130) further includes a tape (170) housed within the housing with the dry stick (180a, 180b, 180c) fixed on the tape (170), and
wherein the needle (350) is configured to be inserted into the aperture (135) of the cassette (130) upon movement of the position adjustment mechanism (510) from the first position to the second position to thereby adjust the needle (350) from i) the retracted position (α) with the needle (350) located above the aperture (135) and above the dry stick (180a, 180b, 180c) to ii) the extended position (β) with the needle inserted through the aperture (135) for flushing the milk sample through the needle (350) into the evacuator (195).

9. The dosing module (137) according to claim 1,
wherein the milk insertion connection (340) is arranged to receive the milk sample from a milk line (110); and
wherein the dosing module (137) comprises a return conduit (198), the return conduit (198) arranged to convey liquid from the evacuator (195) back to the milk line (110), a waste container, or a drain.

10. The dosing module (137) according to claim 1, wherein the motor connection (520) of the position adjustment mechanism (510) is configured to cooperate with an external linear motor (610) such that operation of the external linear motor moves the position adjustment mechanism (510) between the first position and the second position.

11. The dosing module (137) according to claim 10, wherein the motor connection (520) of the position adjustment mechanism (510) comprises a ball joint (520).

12. The dosing module (137) according to claim 1 in combination with the service module (120) and the cassette (130), wherein the first cover section (500) comprises fasteners (530a, 530b, 530c, 530d) that attach the dosing module (137) onto the service module (120), and wherein the cassette (130) is inserted into the service module (120).

13. The dosing module (137) according to claim 12, wherein the fasteners (530a, 530b, 530c, 530d) comprise a snap fit arrangement.

14. The dosing module (137) according to claim 1 in combination with the cassette (130) housing the dry stick (180a, 180b, 180c),
wherein the cassette (130) is comprised of a housing having an aperture (135),
wherein the cassette (130) further includes a tape (170) housed within the housing with the dry stick (180a, 180b, 180c) fixed on the tape (170),
wherein the needle (350) is configured to be inserted into the aperture (135) of the cassette (130) upon movement of the position adjustment mechanism (510) from the first position to the second position to thereby adjust the needle (350) from i) the retracted position (α) with the needle (350) located above the aperture (135) and above the dry stick (180a, 180b, 180c) to ii) the extended position (β) with the needle inserted through the aperture (135) for flushing the milk sample through the needle (350) into the evacuator (195), and
wherein the dosing module further comprises
a dilutant insertion connection (365) arranged to receive dilutant;
a mixing chamber (355) arranged to receive the milk sample from the milk insertion connection (340) and receive the dilutant from the dilutant insertion connection (365); and a second pump (612) configured to provide the dilutant from the dilutant insertion connection (365) to the mixing chamber (355), wherein, the first pump (611) is configured to provide the milk sample from the milk insertion connection (340) to the mixing chamber (355), and the needle (350) is configured to receive a mixture of the milk sample and the dilutant from the mixing chamber (355), and apply the mixture to the dry stick (180a, 180b, 180c), wherein the milk insertion connection (340) is arranged to receive the milk sample from a milk line (110), the dosing module (137) comprising a return conduit (198), the return conduit (198) arranged to convey liquid from the evacuator (195) back to the milk line (110), a waste container, or a drain.

15. The dosing module (137) according to claim 14 in combination with the cassette (130) housing the dry stick (180a, 180b, 180c), wherein at least one of the first pump (611) and the second pump (612) comprises a positive displacement pump.

16. The dosing module (137) according to claim 15 in combination with the cassette (130) housing the dry stick (180a, 180b, 180c), wherein at least one of the first pump (611) and the second pump (612) comprises a peristaltic pump.

17. The dosing module (137) according to claim 15 in combination with the cassette (130) housing the dry stick (180a, 180b, 180c) and in combination with the service module (120), wherein the service module includes a linear motor (610), wherein the motor connection (520) of the position adjustment mechanism (510) is connected with the linear motor (610) such that operation of the linear motor moves the position adjustment mechanism (510) between the first position and the second position to thereby adjust the position of the needle (350) between the retracted position (α) located above the aperture (135) and above the dry stick (180a, 180b, 180c) and the extended position (β).

18. The dosing module (137) according to claim 17 in combination with the cassette (130) housing the dry stick (180a, 180b, 180c) and in combination with the service module (120), wherein the motor connection (520) of the position adjustment mechanism (510) comprises a ball joint (520).

19. The dosing module (137) according to claim 17 in combination with the cassette (130) housing the dry stick (180a, 180b, 180c) and in combination with the service module (120), wherein the first cover section (500) comprises fasteners (530a, 530b, 530c, 530d) that attach the dosing module (137) onto the service module (120), and wherein the cassette (130) is inserted into the service module (120).

20. The dosing module (137) according to claim 17 in combination with the cassette (130) housing the dry stick (180a, 180b, 180c) and in combination with the service module (120), wherein the first cover section (500) is connected to the second cover section (600), the first and second cover sections (500, 600) enclosing the first pump (611), the second pump (612), the evacuator (195), and tubings.

* * * * *